(12) United States Patent
Hartley

(10) Patent No.: US 8,541,743 B2
(45) Date of Patent: Sep. 24, 2013

(54) APPARATUS AND METHOD FOR DETECTING AND QUANTIFYING ANALYTES IN SOLUTION

(71) Applicant: Roc8Sci Co., Arcadia, CA (US)

(72) Inventor: Frank Thomas Hartley, Arcadia, CA (US)

(73) Assignee: ROC8SCI Co., Arcadia, CA (US)

( * ) Notice: Subject to any disclaimer, the term of this patent is extended or adjusted under 35 U.S.C. 154(b) by 0 days.

(21) Appl. No.: 13/668,479

(22) Filed: Nov. 5, 2012

(65) Prior Publication Data

US 2013/0075614 A1    Mar. 28, 2013

Related U.S. Application Data

(63) Continuation-in-part of application No. 13/196,340, filed on Aug. 2, 2011, now Pat. No. 8,344,323.

(51) Int. Cl.
*G01J 5/02*    (2006.01)

(52) U.S. Cl.
USPC ................................. 250/339.07; 250/341.1

(58) Field of Classification Search
USPC ................... 250/340, 338.1, 339.07, 339.03, 250/339.04
See application file for complete search history.

(56) References Cited

U.S. PATENT DOCUMENTS

| | | | |
|---|---|---|---|
| 4,975,581 A * | 12/1990 | Robinson et al. | 250/339.09 |
| 5,170,056 A * | 12/1992 | Berard et al. | 250/341.2 |
| 6,240,306 B1 | 5/2001 | Rohrscheib et al. | |
| 6,646,264 B1 * | 11/2003 | Modiano et al. | 250/339.07 |
| 7,088,441 B2 | 8/2006 | Nahum et al. | |
| 7,961,310 B1 * | 6/2011 | Milosevic | 356/246 |
| 2002/0033453 A1 | 3/2002 | Sauer et al. | |
| 2004/0155668 A1 * | 8/2004 | Hajduk et al. | 324/663 |
| 2007/0075281 A1 * | 4/2007 | Gunning et al. | 250/573 |
| 2008/0230698 A1 * | 9/2008 | Simelgor et al. | 250/338.1 |
| 2011/0009720 A1 * | 1/2011 | Kunjan et al. | 600/316 |

OTHER PUBLICATIONS

Boosalis, Fani Polyzos, "U.S. Appl. No. 13/196,340 Office Action", Jan. 20, 2012, Publisher: USPTO, Published in: US.
Boosalis, Fani Polyzos, "U.S. Appl. No. 12/157,513 Notice of Allowance May 18, 2011", , Publisher: USPTO, Published in: US.
Boosalis, Fani Polyzos, "U.S. Appl. No. 12/157,513 Office Action Mar. 18, 2011", , Publisher: USPTO, Published in: US.

* cited by examiner

*Primary Examiner* — David Porta
*Assistant Examiner* — Faye Boosalis
(74) *Attorney, Agent, or Firm* — Kaplan Bryer Schwarz & Ottesen, LLP

(57) ABSTRACT

A method for identifying and quantifying one or more analytes included in a sample comprising a background solvent is disclosed. The present invention locates a sample fluid at a sample region by virtue of a sample holder that comprises work-hardened silver halide. The sample fluid at the sample region is then spectrally characterized via a mid-infrared spectrometer.

30 Claims, 6 Drawing Sheets

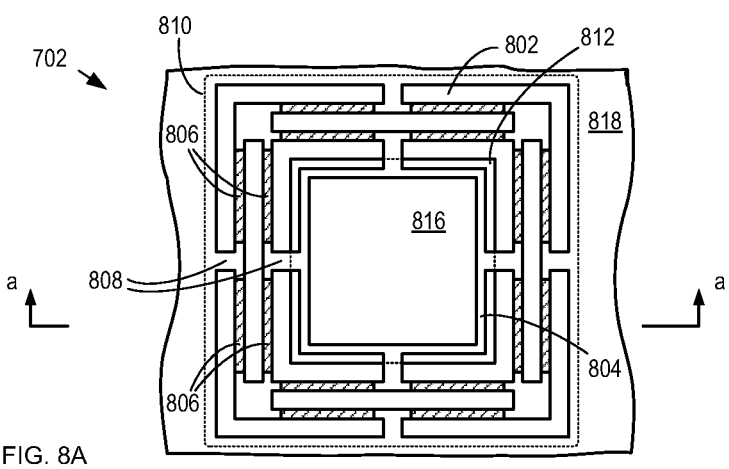
FIG. 8A
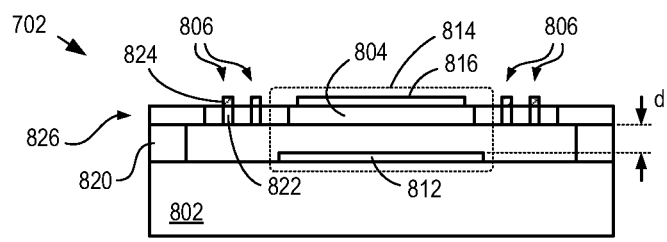
FIG. 8B view through line a-a

APPARATUS AND METHOD FOR DETECTING AND QUANTIFYING ANALYTES IN SOLUTION

CROSS REFERENCE TO RELATED APPLICATIONS

This case is a continuation-in-part of co-pending U.S. patent application Ser. No. 13/196,340, entitled "Apparatus and Method for Detecting and Quantifying Analytes in Solution," filed on Aug. 2, 2011, which is a continuation-in-part of U.S. patent application Ser. No. 12/157,513 (now U.S. Pat. No. 8,022,036), filed Jun. 11, 2008, which claimed the priority of U.S. Provisional Patent Application 60/933,969, filed Jun. 11, 2007, each of which is incorporated herein by reference in its entirety.

FIELD OF THE INVENTION

The present invention relates to chemical analysis in general, and, more particularly, to analyte detection and analysis using spectrometry.

BACKGROUND OF THE INVENTION

An ability to quickly identify and quantify one or more analytes in a solution is desirable in many areas, including medical diagnostics, petroleum exploration, environmental health monitoring, and drug testing. Unfortunately, many conventional analysis systems and methods are time-intensive and can be quite complicated. In addition, many conventional analytical approaches require the use of consumable reagents or test strips, which require calibration for each use, are subject to degradation over time, often provide only a qualitative result, and can require coding.

Infrared spectroscopy represents an optical chemical analysis method that overcomes many of these drawbacks. Infrared spectroscopy interrogates a sample using an optical signal having a relatively broad wavelength range. Infrared light (electromagnetic radiation having a wavelength within the range of approximately 740 nanometers to approximately 300 microns) is typically transmitted through the sample such that each chemical constituent in the sample imparts spectral information on the outgoing optical signal. This spectral information manifests as intensity peaks at specific wavelength locations in a spectral plot of the output signal, wherein the positions, magnitudes, and inflections of these peaks (i.e., the "spectral fingerprint") are indicative of the constituent chemicals in the sample.

Initially developed for use in outer space exploration, spectral fingerprinting based on spectroscopy (infrared- and/or visible-light spectroscopy) has been used to measure Doppler shifts caused by radial velocity changes of distant suns in the search for exo-planets potentially orbiting around them. In order to effectively measure such small effects, however, a spectrometer requires careful calibration and an absolute wavelength reference. In space applications, iodine is often used for these purposes. Iodine is an attractive reference because a temperature-controlled iodine vapor cell is spectrally rich over a useful wavelength range. Specifically, iodine has sixty-seven precise and non-variant spectral features over the wavelength range from 389.5 nanometers (nm) to 681.5 nm. An iodine vapor cell is added to the optical path of the interferometer so that the light from the distant sun can pass through it. The spectral features in the light from the sun are then verniered against the iodine spectral features. The Doppler shift of the sun's spectra, therefore, can be precisely determined relative to the absolute locations of the spectral features of the iodine.

The medical industry has embraced infrared spectroscopy for some analytical applications, such as blood analysis, blood flow kinetics, brain scanning, and the like. Unfortunately, infrared spectroscopy, as conventionally practiced, has several drawbacks.

First, the typical analytes of interest normally exist at extremely low concentrations (parts-per-million or even lower concentrations) in a body fluid or blood, the bulk of which (approximately 80%) is water. Typically, the spectral characteristics of the water swamp the relatively small spectral contributions of the targeted analytes, which makes it extremely difficult to identify and/or quantify the analytes.

Second, although much of the analyte-specific spectral information is located in the mid-infrared wavelength range (i.e., 2.5 microns to 12.5 microns), water has a high absorption coefficient in this wavelength range. As a result, prior-art infrared spectroscopy systems have focused on the near infrared wavelength range (i.e., infrared wavelengths<2.5 microns) to mitigate signal attenuation due to water absorption.

Third, interference from protein and water absorption spectra typically precludes univariant calibration that would enable quantification of analytes present in a bodily fluid. Further, in many such applications, the use a separate calibration chemical in the analysis of a chemical mixture is highly undesirable. Still further, in many cases, the addition of more spectral information by using a calibration chemical would often serve only to further confound the analysis of the sample.

A common approach to mitigate some of these issues and enable some quantification of the analytes is to collect the blood (or other bodily fluid) so that it can be held in a container of known thickness during analysis. This enables the estimation of the concentration of the analyte that is based on the known path length of the infrared light through the sample. The need to draw blood increases patient discomfort and anxiety, however. It also represents a potential health risk to the caregiver. Ideally, blood analysis would be performed non-invasively by transmitting the infrared radiation through a thin-tissue region of the body, such as the ear lobe or webbing between the fingers. Unfortunately, it is extremely difficult to quantify the measured analytes in the blood in such systems due to the fact that the precise path length of the light through the tissue is indeterminate.

Infrared spectroscopy fluid analysis has applicability to many applications outside of medicine as well, such as remote sensing, industrial process control, environmental monitoring, pollution control, and criminology. Some such applications require an ability to monitor analytes in background solvents other than water. In addition, many require a sensor system suitable for operation in extremely harsh conditions. For example, distributed sensors can be used to more effectively control chemical or drug synthesis systems, thereby increasing product quality, lowering costs, and reducing generation of undesirable chemical byproducts. Further, remote sensors having improved sensitivity and accuracy can improve geological exploration, detection of enemy activity, and detection of treaty violations using, for example, unmanned vehicles such as drones. Of course, water-based non-medical applications exist as well, such the accurate detection and quantification of analytes in groundwater or industrial plant effluent, which would enable better detection of drinking water contamination, faster detection of industrial plant effluent pollution, or detection of impurities due to fracking operations, thereby improving public safety, improving environmentally friendly energy generation, and protecting the environment.

An ability to quantify one or more analytes in a background solution high accuracy and throughput would represent a significant advance of the state-of-the-art.

SUMMARY OF THE INVENTION

The present invention enables identifying and quantifying one or more analytes in solution containing a background solvent. Embodiments of the present invention are particularly well suited for use medical diagnostics, environmental monitoring, industrial process control, pollution control, and remote chemical sensing, among others.

An illustrative embodiment of the present invention is a spectrometer that interrogates a fluid in a sample cell using mid-infrared radiation, wherein the sample cell is formed of work-hardened silver halide. The sample cell is substantially transparent for mid-infrared radiation. The sample cell introduces a sample containing one or more analytes in a background solvent into the spectrometer, which interrogates the sample to identify and quantify at least one of the analytes. In some embodiments, the sample cell is suitable for use in harsh chemical environments.

The spectrometer includes a mid-infrared radiation source that is driven with an electrical pulse train so that it emits pulses of mid-infrared radiation having a wavelength within the range of 2.5 microns to approximately 12.5 microns. This radiation is directed through the sample cell to produce an optical signal containing spectral components of both the analyte and the background solvent. A wavelength discriminator then distributes this composite optical signal into discrete wavelength signals, each having a spectral width of approximately 2-3 nm. Each discrete wavelength signal is received by a different one of a plurality of MEMS-based detectors having a capacitance that is based on the intensity of the radiation incident upon it. Electronic circuits coupled with the detectors convert these capacitances into a composite spectral signal that represents the total chemical makeup of the first sample.

A processor receives the composite spectral signal and effectively removes the spectral contribution of the background solvent from the composite spectral signal by applying a pre-determined spectral model of the background solvent as a spectral template. The processor substantially subtracts this spectral template from the composite spectral signal to substantially isolate the spectral contribution from the analytes as an output spectral signal. In other words, the "noise" in the composite spectral signal (corresponding to the background solvent) is reduced, thereby yielding an output signal having an improved signal-to-noise ratio.

In some embodiments, each MEMS-based detector comprises a plate having an absorbing region and an underlying electrode that is disposed on a substrate. The plate and electrode collectively define a parallel-plate capacitor whose capacitance is based on their separation. In operation, the absorbing region receives one of the wavelength signals and converts its optical energy into heat. The plate is thermally coupled with an actuator whose temperature determines the separation between the plate and the electrode. As a result, heat conveyed into the actuator from the absorbing region changes the temperature of the actuator, which, in response, changes the separation between the plate and electrode. In order to enable rapid response of the actuator, the actuator is also thermally coupled with the substrate to facilitate removal of the heat from the actuator. In some embodiments, the plate and a portion of the actuator comprise diamond, which has a high thermal conductivity.

In some embodiments, the spectrometer does not include a sample cell, but is arranged to interrogate tissue held in an area between the mid-infrared source and the wavelength discriminator and MEMS-based detector. In some embodiments, tissue is held between an input optical fiber and an output optical fiber, wherein each of the input and output optical fibers is made of a material that is substantially transparent for mid-infrared radiation. In some embodiments, at least one of the optical fibers comprises silver halide.

An embodiment of the present invention comprises (1) a spectrometer comprising; (i) a source operable for providing mid-infrared radiation to a sample region; (ii) a wavelength discriminator operable for receiving a composite light signal from the sample region and spatially dispersing the composite light signal as a plurality of wavelength signals; and (iii) a plurality of detectors, each of the plurality of detectors operable for generating one of a plurality of first electrical signals based on one of the plurality of wavelength signals; and (2) a sample holder, the sample holder being operable for locating a sample fluid at the sample region, the sample holder being dimensioned and arranged to enable the sample fluid to receive mid-infrared radiation and provide the composite light signal.

BRIEF DESCRIPTION OF THE DRAWINGS

FIGS. 8A and 8B depict schematic drawings of top and side views, respectively, of a detector in accordance with the illustrative embodiment of the present invention.

DETAILED DESCRIPTION

Figure 1:
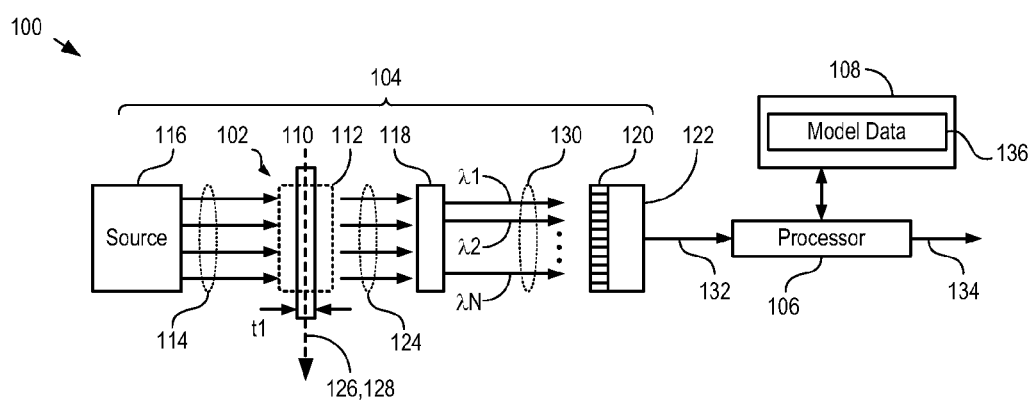
FIG. 1 depicts a schematic drawing of a chemical analysis system in accordance with an illustrative embodiment of the present invention.

The present invention enables rapid, high-confidence detection and quantification of low-concentration analytes in a background solvent. Some embodiments of the present invention are particularly well suited for medical applications and environmental testing applications, wherein analysis of analytes in a water-rich environment is desired. Other embodiments of the present invention are well suited to industrial, chemical, and petrochemical applications, wherein analysis of analytes in a background solvent other than water is desired.

The present invention enables remote sensing using mid-infrared spectrometry. Embodiments of the present invention are particularly well suited for use in such applications as remote diagnostic systems that can effectively and quickly detect and quantify analytes in a water-rich environment. Some embodiments, of the present invention enable interrogation of a sample using mid-infrared radiation conveyed to the sample site via optical fibers suitable for use at mid-infrared wavelengths. As a result, the mid-infrared source and detector can be housed remotely from the sensor sample head, enabling protection of the source and detector from harsh environmental conditions.

Exemplary applications for embodiments of the present invention include, without limitation:
  i. industrial process control, wherein it is desirable to monitor chemical compositions of fluids flowing through conduits at different points in a system;
  ii. environmental monitoring, such as continuous testing of water supply industrial flow effluent;
  iii. reaction by-product quality control;
  iv. on-site forensic crime-scene analysis;
  v. geological exploration;
  vi. monitoring military activity; and
  vii. medical diagnostics.

The use of mid-infrared radiation affords embodiments of the present invention with significant advantages over chemical analysis systems of the prior art. For the purposes of this Specification, including the appended claims, "mid-infrared radiation" is defined as electromagnetic radiation having a wavelength within the range of approximately 2.5 microns to approximately 12.5 microns.

In the prior art, mid-infrared radiation is typically avoided for chemical analysis in spectrometry-based systems because many host materials (e.g., solvent fluids, blood, saline, bodily tissue, etc.) have a well-known absorption window in the mid-infrared wavelength range. Because of this absorption window, mid-infrared radiation does not significantly penetrate sample material in many applications, such as blood serum analysis, glucose monitoring, and the like.

Prior-art systems, therefore, are typically based on near-infrared light (i.e., wavelengths within the range of approximately 800 nm to approximately 2500 nm), where light does penetrate sample material to a usable depth. Unfortunately, the spectral information from target chemicals and compounds in a sample is typically overwhelmed by the background spectral information associated with the host material. In fact, the identification and quantitative analysis of target analytes and chemicals is precluded by the fact that their signature information is simply "lost in the noise" of spectral information of the host material.

As discussed in the parent application, embodiments of the present invention access the wealth of spectral information for a target chemical that exists the mid-infrared "fingerprint" region of the electromagnetic spectrum by effectively removing the "known" spectrum of the host material from the composite spectrum of the sample. Once the spectral information of the host material is effectively removed, the spectral information for included analyte or analytes can be readily analyzed to identify and quantify these target chemicals.

In addition, the reliance on near-infrared light in the prior art enables avoidance of the challenges associated with providing sample cells, optical fibers, etc., that are substantially transparent for radiation having a wavelength within the range of 2.5 to 12.5 microns.

It is an aspect of the present invention, therefore, that optical access to sample fluids can be achieved by forming sample holders comprising structural components made of material that is substantially transparent to mid-infrared radiation—specifically, work-hardened silver halide. As discussed below, such sample holders can be formed to enable real-time analysis of sample material as it flows through a sample region, analysis of a fixed amount of sample fluid as it is held in the sample region, or remote interrogation of a sample fluid via optical fibers formed of material that is substantially transparent for mid-infrared radiation.

FIG. 1 depicts a schematic drawing of a chemical analysis system in accordance with an illustrative embodiment of the present invention. System 100 comprises sample cell 102 spectrometer 104, processor 106, and database 108. In the illustrative embodiment, system 100 is a blood-analysis system for quantifying glucose in a blood sample (i.e., sample fluid 110).

Figure 2:
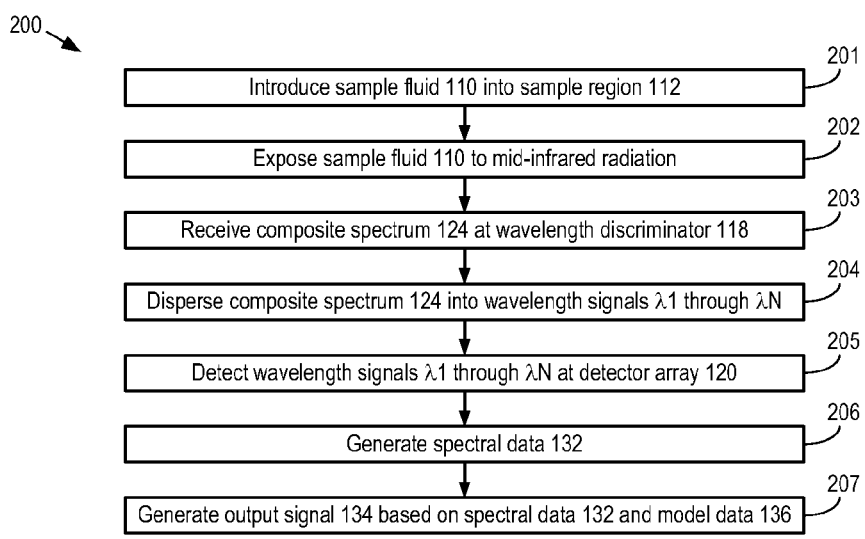
FIG. 2 depicts operations of a method suitable for remotely detecting and quantifying an analyte in accordance with the illustrative embodiment of the present invention.

FIG. 2 depicts operations of a method suitable for remotely detecting and quantifying an analyte in accordance with the illustrative embodiment of the present invention. Method 200 begins with operation 201, wherein sample cell 102 introduces sample fluid 110 into sample region 112 of spectrometer 104. Method 200 is described herein with continuing reference to FIG. 1 as well as reference to FIGS. 2-7.

Figure 3:
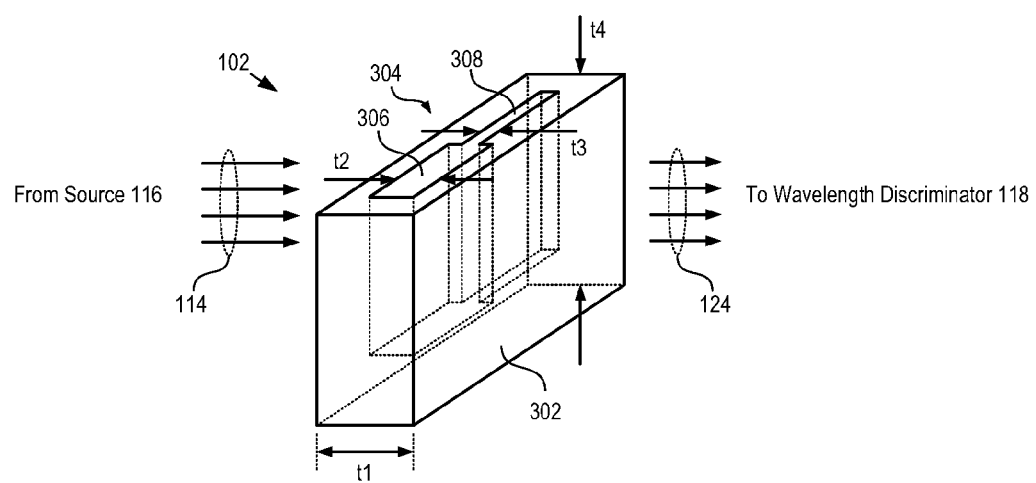
FIG. 3 depicts a schematic drawing of a perspective view of a sample holder in accordance with the illustrative embodiment of the present invention.

FIG. 3 depicts a schematic drawing of a perspective view of a sample holder in accordance with the illustrative embodiment of the present invention. Sample holder 102 is a cuvette comprising housing 302 and reservoir 304.

Housing 302 is a rectangular block of silver halide (AgCl$_x$Br$_{1-x}$) having a thickness of t1 in the direction of propagation of mid-infrared radiation 114. A thickness of t1 is selected so as to provide suitable mechanical robustness to housing 302. In some embodiments, housing 302 comprises a different material that is substantially transparent for mid-infrared radiation 114.

Reservoir 304 is a fixed-volume chamber for holding sample fluid 110. Reservoir 304 includes sub-chamber 306 and sub-chamber 308. Sub-chamber 306 has a uniform width of t2 along the direction of propagation of light 110, where t2 is selected to facilitate drawing fluid into reservoir 304 via capillary action. Sub-chamber 308 has a uniform width t3 along the direction of propagation of light 110, where t3 is selected such that sub-chamber 308 acts as a physical barrier to red and white blood cells. As a result, reservoir 304 enables passive, mechanical separation of blood cells from plasma within sample fluid 110.

In some embodiments, sample holder 102 includes a projection, or "tongue" that extends from sub-chamber 306 and/or sub-chamber 308. This tongue includes a fluidic channel having similar dimensions to sub-chamber 306 such that the tongue facilitates the drawing of sample fluid 110 into sub-chambers 306 and 308.

In the illustrative embodiment, sample holder 102 is formed by pressure-forming a silver halide block with a pressing spade to form reservoir 304 and work harden the silver halide material.

Figure 4:
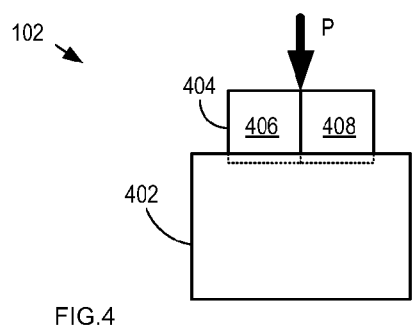
FIG. 4 depicts a schematic drawing of a cross-sectional view of sample holder during formation in accordance with the illustrative embodiment of the present invention.

FIG. 4 depicts a schematic drawing of a cross-sectional view of sample holder during formation in accordance with the illustrative embodiment of the present invention. Formation of sample holder 102 begins with the extrusion of a solid bar of silver halide using a conventional extrusion system. Once formed, the solid bar is cut into lengths equal to t4, the desired height of sample holder 102, to form solid silver halide block 402.

Reservoir 304 is formed in block 402 by pressing spade 404 into the block with force P while block 402 is rigidly held by a holder (not shown for clarity).

Spade 404 is a conventional piston-driven ram having sections 406 and 408, which have thicknesses t2 and t3, respectively.

By forcing spade 404 into block 402, a depression the size of reservoir 304 is formed. Simultaneously, the silver halide material of the block is work hardened by the compression of the silver halide material.

It will be clear to one skilled in the art, after reading this Specification, that system 400 is merely one example of a system suitable for forming a work-hardened silver halide sample cell. For example, silver halide structures can be work hardened via mechanical apparatus including, without limitation, mechanical presses, die cast systems, and the like. Further, although system 400 produces a fixed-volume sample holder, it will be clear to one skilled in the art, after reading this Specification, how to make and use alternative embodiments of the present invention wherein an extrusion system is used to form solid rods, conduits, optical fibers, or other similar structures.

It should be noted that silver halide is not typically considered a suitable material for a structural element, such as sample holder 102, due to the fact that the hardness of silver halide is normally similar to that of lead. In a non-work-hardened state, for instance, sample holder 102 would likely collapse under the capillary forces that draw sample fluid 110 into reservoir 304. It is an aspect of the present invention, however, that silver halide can be work hardened to a hardness that enables its use in a structural element, as described above. This affords embodiments of the present invention significant advantage over prior-art chemical analysis systems. First, silver halide crystals are relatively inexpensive relative to other materials transparent for mid-infrared radiation. Second, silver halide crystals can be work hardened at relatively low cost, which means that work-hardened silver halide structures can be made relatively easily and inexpensively. Third, silver halide exhibits little or no attenuation for light within the wavelength range of approximately 2 microns to approximately 25 microns. Over this wavelength range, silver halide has a propagation loss of less than 0.2 dB per meter. Fourth, silver halide is non-toxic for humans, non-hygroscopic, and biocompatible.

Although work-hardened silver halide is the preferred material for sample cell 102, it will be clear to one skilled in the art, after reading this Specification, how to specify, make, and use alternative embodiments of the present invention comprising sample cells made of another material that is substantially transparent for mid-infrared radiation. Other materials suitable for use in the present invention include, without limitation, fused silica, fluoride glasses, chalcogenide glasses, and the like.

At operation 202, spectrometer 104 interrogates sample fluid 110 with mid-infrared radiation 114.

The uniform width of the sub-chambers of reservoir 304 enables spectrometer 104 to interrogate a known amount of material in each of sub-chambers 306 and 308. In some embodiments, this facilitates determination of the concentration of one or more analytes in the sample fluid.

In some embodiments, the sample cell is a portion of a conduit that enables sample fluid 110 to flow through sample region 112, wherein the mid-infrared radiation passes through a known thickness of sample fluid. Suitable conduits comprise a material that is substantially transparent to mid-infrared radiation, such as silver halide.

Spectrometer 104 comprises source 116, wavelength discriminator 118, detector array 120, and detector circuitry 122. System 100 employs infrared radiation to optically interrogate sample material and generate spectral information that is characteristic of one or more analytes in the sample. For exemplary purposes, system 100 is described herein as a chemical analysis system for detecting and quantifying glucose in a blood sample.

Mid-infrared radiation 114 is provided to sample region 112 by source 116.

Figure 5:
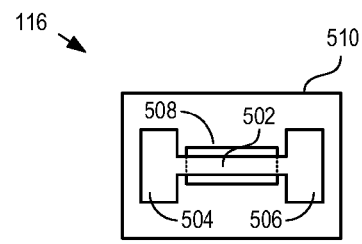
FIG. 5 depicts a schematic drawing of a top view of a mid-infrared source in accordance with the illustrative embodiment of the present invention.

FIG. 5 depicts a schematic drawing of a top view of a mid-infrared source in accordance with the illustrative embodiment of the present invention. Source 116 comprises filament 502 and terminals 504 and 506.

Filament 502 is a beam of silicon carbide having a thickness of approximately 2 microns, a width of approximately 5 microns, and a length of approximately 30 microns.

Filament 502 is suspended above cavity 508, which is formed in substrate 510. Filament 502, cavity 508, and terminals 504 and 506 are formed on substrate 510 using conventional surface micromachining techniques. In response to a flow of electrical current between terminals 504 and 506 (i.e., through filament 502), filament 502 becomes hot and emits mid-infrared radiation.

The materials of source 116 and the dimensions of filament 502 described herein in are merely exemplary and it will be clear to one skilled in the art, after reading this Specification, that source 116 and filament 502 can have a wide range of dimensions and/or comprise any of a wide range of suitable materials including, without limitation, metals, semiconductors, silicon, single-crystal silicon, graphite, dielectrics, and the like.

One skilled in the art will recognize that an uncooled infrared detector is well suited for detecting a change in the intensity of incident infrared radiation; however, it is typically poorly suited to sensing the absolute intensity level of received infrared radiation. As a result, it has been typical in the prior art to modulate the infrared radiation that is received by such a detector by means of an external modulator, such as a mechanical beam-chopper (e.g., a rotating blade, mechanical shutter, etc.). Mechanical beam-choppers, however, are relatively large, costly, and represent a reliability issue.

Further, prior-art systems typically employ a conventional incandescent light or specialty lamp that emits near-infrared light. Unfortunately, such conventional infrared sources emit light over too wide a wavelength range. As a result, light outside the measurement wavelength range generates spectral noise by parasitic heating of components of the system. This spectral noise degrades the sensitivity and accuracy of prior-art systems. In some prior-art systems spectral filters are included to narrow the emission bandwidth of their infrared sources.

By virtue of the small size of its emissive filament, however, source 116 can exhibit all of the desired characteristics of an externally modulated, spectrally narrow, infrared source without the added cost and complexity associated with external modulation and added wavelength filters. Since filament 502 has very low thermal mass, its temperature closely tracks the magnitude of electrical current that flows through it. Direct modulation of filament 502, therefore, can be used to induce it to emit a modulated optical signal directly. In some embodiments, electrical pulse shaping and current regulation are also used to further enable filament 502 to provide a high radiant output having a high temperature-slew rate, little or no thermal hysteresis, and extremely low power consumption.

In order to avoid time delays associated with the heating and cooling of a cover window, in some embodiments, an optical window or other protective cover plate does not cover filament 502. In some applications, however, it is necessary to protect the filament and a suitable, substantially transparent cover window is positioned over filament 502. It is an aspect of the present invention that such a cover window can be formed using work-hardened silver halide, or equivalent material.

It should be noted that blood is merely an example of a sample material for which the present invention is applicable and, therefore, is useful for describing the illustrative embodiment. The present invention is suitable for identification and/or quantification of analytes contained in a wide range of liquid solvents, such as water, saline, oils, alcohols, acids, and the like. Sample materials for which the present invention is applicable include, without limitation, petroleum products, saliva, bodily fluids, bodily tissue, biological matter, sera, pharmaceutical products, water, and the like.

At operation 203, wavelength discriminator 118 receives composite spectrum 124 from sample region 112. Composite spectrum 124 includes spectral information of background solvent 126 and analyte 128, as well as other analytes that might be included in sample fluid 110.

It should be noted that the illustrative embodiment, sample cell 102 places sample fluid 110 in sample region 112 such that light 114 is transmitted through sample fluid 110 to produce composite spectrum 124; however, it will be clear to one skilled in the art, after reading this specification, how to specify, make, and use alternative embodiments of the present invention wherein composite spectrum 124 is reflected from sample fluid 110 to wavelength discriminator.

At operation 204, wavelength discriminator 118 spatially disperses the wavelength components of composite spectrum 124 as a plurality of wavelength signals.

Figure 6:
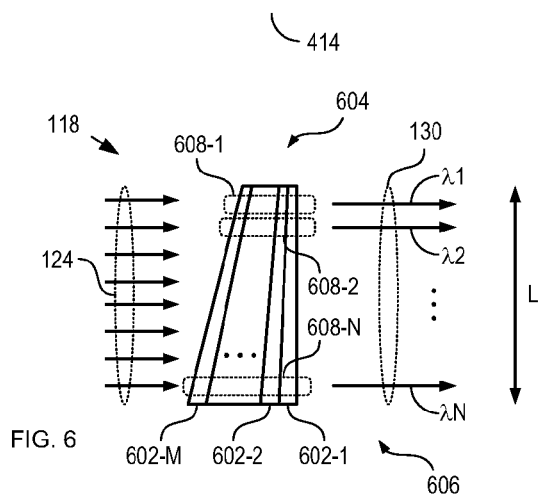
FIG. 6 depicts a schematic drawing of a cross-sectional view of a wavelength separator in accordance with the illustrative embodiment of the present invention.

FIG. 6 depicts a schematic drawing of a cross-sectional view of a wavelength separator in accordance with the illustrative embodiment of the present invention. Wavelength discriminator 118 is a spatial wavelength filter that receives composite spectrum 124 and provides wavelength signal 130. Wavelength signal 130 comprises wavelength signals $\lambda 1$ through $\lambda N$. In order to effectively detect and quantify many analytes, system 100 must be able to differentiate spectral signals with a granularity of approximately 2 wave numbers over the 10 micron-wide spectral range from 2.5 to 12.5 microns. Wavelength separator, therefore, separates composite spectrum 124 into thousands of individual wavelength signals.

Wavelength discriminator 118 comprises layers 602-1, through 602-M (referred to, collectively, as layers 602), which are alternating layers of silicon dioxide and silicon nitride. The thickness of each of layers 602 increases linearly along length, L, from end 604 to end 606. The thickness of each of layers 602 at end 604 is equal to one-quarter of wavelength $\lambda 1$ (within the material of each layer). In similar fashion, the thickness of each of layers 602 at end 606 is equal to one-quarter of wavelength $\lambda N$. As a result, layers 602 collectively define a linear array of wavelength filters 608-1 through 608-N (referred to, collectively, as wavelength filters 608) that are equally spaced along length, L. Each of wavelength filters 608 passes only one of wavelength signals $\lambda 1$ through $\lambda N$ and blocks transmission of the remainder of composite spectrum 124. For example, wavelength filter 608-1 passes only wavelength $\lambda 1$, wavelength filter 608-2 passes only wavelength $\lambda 2$, etc. As a result, wavelength discriminator 118 provides a linear array of wavelength signals where each wavelength signal uniquely includes one spectral slice of composite spectrum 124.

Although in the illustrative embodiment, layers 602 are alternating layers of silicon dioxide and silicon nitride, one skilled in the art will recognize that the materials used for layers 602 can be selected from a myriad of alternative materials.

In order to obtain suitable wavelength granularity, the finesse of each of wavelength discriminators 118 is within the range of approximately 2 nm to approximately 3 nm. As a result, in some embodiments, wavelength discriminator 118 comprises many layers 402. In some cases, in fact, the number of layers, M, exceeds 1000.

Although the illustrative embodiment comprises a wavelength separator that is a multi-layer wedge filter, it will be clear to one skilled in the art, after reading this specification, how to specify, make, and use alternative embodiments of the present invention wherein wavelength discriminator 118 is other than a multi-layer wedge-filter. Wavelength separators suitable for use with the present invention include, without limitation: wavelength dispersive elements, such as prisms, diffraction gratings, holographic elements; wavelength filter elements, such as discrete wavelength filter arrays, tunable filter arrays; and combinations thereof, such as tunable diffractive gratings, rotatable diffraction gratings, rotatable prisms, and the like.

At operation 205, each of wavelength signals $\lambda 1$ through $\lambda N$ is detected by a different element of detector array 120.

Figure 7:
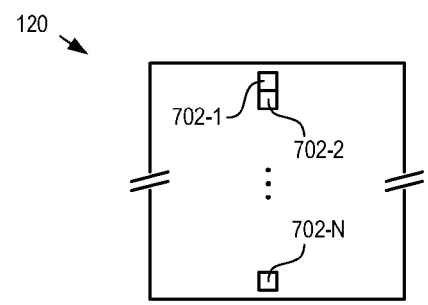
FIG. 7 depicts a schematic drawing of a top view of a detector array in accordance with the illustrative embodiment of the present invention.

FIG. 7 depicts a schematic drawing of a top view of a detector array in accordance with the illustrative embodiment of the present invention. Detector array 120 comprises detectors 702-1 through 702-N (referred to, collectively, as detectors 702). Each detector 702 comprises a capacitor whose capacitance is based on the intensity of light incident upon it. In some embodiments, each detector 702 is substantially thermally and mechanically isolated from its neighboring detectors to mitigate thermal and mechanical crosstalk.

Detectors 702 are arranged such that each detector receives a different one of wavelength signals $\lambda 1$ through $\lambda N$.

FIGS. 8A and 8B depict schematic drawings of top and side views, respectively, of a detector in accordance with the illustrative embodiment of the present invention. Detector 702 is a capacitive sensor whose capacitance depends on the separation between a center region of a membrane and an electrode located on an underlying substrate. This separation is, in turn, based on the intensity of radiation that is incident on the detector. Detector 702 comprises substrate 802, plate 804, elements 806, and tethers 808.

Substrate 802 is a conventional silicon substrate. In some embodiments, substrate 802 is comprises another material, such as a semiconductor, ceramic, metal, plastic, composite material, glass, and the like. Substrate 802 comprises electrode 812. Electrode 812 is a region of electrically conductive material, such as a metal, that is disposed on substrate 802 directly under plate 804. As a result, plate 804 and electrode 812 collectively define parallel-plate capacitor 814. In some embodiments, electrode 812 is electrically connected to ground potential. In some embodiments, substrate 806 is a metal plate and electrode 812 is a portion of an electrically conductive substrate.

Plate 804, elements 806, and tethers 808 are formed from membrane 810 via conventional Micro-Electro-Mechanical Systems (MEMS) fabrication techniques. Membrane 810 is a portion of layer 826, which is disposed on spacer layer 820, which is further disposed on substrate 802. Layer 826 is a layer of diamond having a thickness of approximately 1 micron. In some embodiments, layer 826 comprises another suitable material that has a relatively high thermal conductivity. In some embodiments, layer 826 has a thickness other than 1 micron. One skilled in the art will recognize that many materials are suitable for use in layer 826.

Plate 804 is a substantially square plate that is held above electrode 812 via elements 806 and tethers 808. Plate 804 and electrode 812 are separated by gap, d, which, in the absence of light, is equal to the thickness of spacer layer 820. Plate 802 has a size suitable for receiving an entire wavelength signal from wavelength discriminator 118 without receiving a significant amount of a second wavelength signal. In some embodiments, plate 804 has a shape other than square. Plate 804 comprises absorber 816. Absorber 816 comprises a material having high absorptivity to enable absorption of mid-IR radiation (e.g., tungsten, etc.). In some embodiments, absorber 816 is a region of plate 804 that has been treated to increase its absorptivity. In some embodiments, plate 804 comprises a material having a relatively high absorptivity and, therefore, absorber 816 is merely a portion of plate 804.

Elements 806 collectively define an actuator that controls the separation, d, between plate 804 and electrode 812. Each of elements 806 comprises a bi-material layer structure comprising tether 822 and material 824, which is disposed on tether 822. Material 824 has a thermal expansion coefficient that differs from that of the material of membrane 810 (and, therefore, tether 822).

Each of tethers 808 is a portion of membrane 810. Tethers 808 collectively mechanically couple plate 808 to elements 806 and mechanically couple elements 806 to field region 818. Field region 818 is disposed on spacer layer 820, which mechanically and thermally couples field region 818 to substrate 802.

In response to a change of temperature of elements 806, a difference in the amount of thermal expansion of the first and second materials induces the elements to change their curvature. As a result, elements 806 either bend upward from substrate 802 or downward toward substrate 802 (depending on the relative thermal expansion coefficients of the two materials and the direction of temperature change). Since each of elements 806 has one end that is fixed at field region 818, this bending changes the height of the opposite end of each of the elements above substrate 802.

In operation, detector 702 receives one of wavelength signals λ1 through λN. Plate 804 converts the energy of the received wavelength signal into thermal energy, heating plate 804. Heat from plate 804 is conducted to elements 806 via tethers 808, increasing the temperature of elements 806. Their increased temperature causes elements 806 to change the separation between plate 804 and electrode 806, changing the capacitance of capacitor 814.

In addition to supporting plate 804 above electrode 812, elements 806 and tethers 808 also thermally couple plate 804 to substrate 802 through field region 818. The materials and dimensions of detector 702 are selected to enable it to response quickly to a change in the intensity of radiation incident upon it. In the illustrative embodiment, for example, detector 702 is designed with a time constant of 15 milliseconds. A fast time constant arises from the fact that membrane 810 is very thin and therefore has a very low thermal capacity. Further, since membrane 810 comprises material having high thermal conductivity, and plate 804, elements, 806, and tethers 808 are thermally coupled; heat readily flows into and out of elements 806 quickly. This provides elements 806 with a rapid physical response to a change in the intensity of incident radiation.

Although in the illustrative embodiment, plate 804, elements 806, and tethers 808 are formed from a substantially continuous membrane, it will be clear to one skilled in the art, after reading this specification, how to specify, make, and use alternative embodiments of the present invention wherein are plate 804, elements 806, and tethers 808 are formed using different surface micromachining techniques. In some embodiments, for example, at least one of plate 804, elements 806, and tethers 808 comprises material that is different than the material of at least one other of these components.

At operation 206, the capacitance of each of detectors 702 is converted by detector circuitry 122 into an electrical signal based on the intensity of the wavelength signal received by that detector. These electrical signals collectively define composite spectral data 132. Detector circuitry 122 comprises a plurality of conventional circuits for converting a capacitance into an electrical signal, such as a circuit typically included in a conventional read-out integrated circuit (ROIC).

At operation 207, processor 106 generates output signal 134 based on composite spectral data 132 and model data 136. In some embodiments, output signal 134 is further based on the pressure of sample fluid 110. Output signal 134 includes identification of analyte 128 and, in some embodiments, an estimation of the concentration of analyte 128 in sample fluid 110.

Processor 106 is a conventional computer processor capable of executing instructions, running programs, and accessing database 108, which is stored in a conventional memory module. In some embodiments, processor 106 comprises the memory module that contains database 108.

Further details of methods suitable for determining the identity and concentration of an analyte in a background solvent can be found in the parent case of this application, U.S. patent application Ser. No. 13/196,340.

Figure 9:
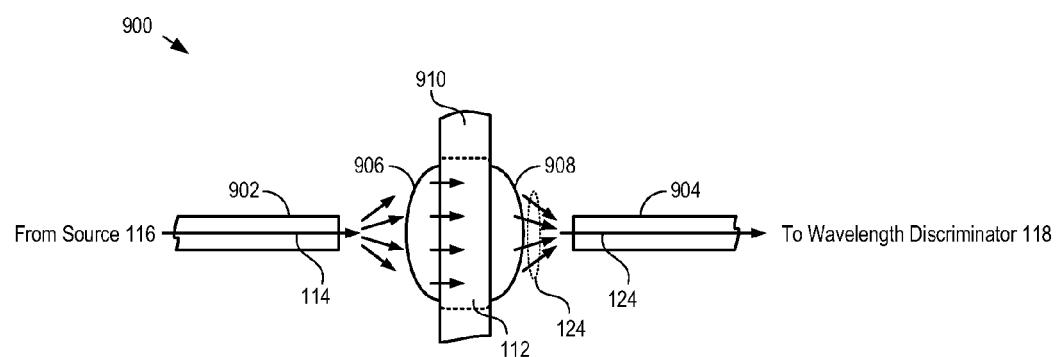
FIG. 9 depicts a schematic drawing of a portion of a chemical analysis system in accordance with a second alternative embodiment of the present invention.

FIG. 9 depicts a schematic drawing of a portion of a chemical analysis system in accordance with a second alternative embodiment of the present invention. System 900 comprises source 116, optical fibers 902 and 904, and lenses 906 and 908. System 900 enables analysis of a sample fluid from a remote location by conveying mid-infrared radiation 114 to sample region 112 and composite signal 124 away from the sample region via optical fibers suitable for operation in the mid-infrared wavelength range.

In this exemplary embodiment, sample region 112 contains a portion of an ear lobe to enable chemical analysis of blood contained within its tissue. Ear lobe 910 is clamped between lenses 906 and 908 via a clamping mechanism (not shown for clarity).

Each of optical fibers 902 and 904 comprises a material that is substantially transparent for mid-infrared radiation—preferably silver halide. Silver halide is well suited to transport of mid-infrared radiation by virtue of its operation spectral range of approximately 2 microns to approximately 25 microns, a low propagation loss of approximately 0.2 dB/meter (for air-cladded fibers), and a refractive index in the range of 1.98 to 2.16. Further, using an extrusion system analogous to that shown above and with respect to FIG. 3, optical fibers of silver halide can be drawn to lengths from 2 meters to 15 meters. Still further, the malleability of non-work-hardened silver halide enables a bending radius as small as 3 mm.

Optical fiber 902 is optically coupled between source 116 and lens 906, which collimates the radiation emitted from the output facet of the optical fiber to flood illuminate sample region 112. As a result, optical fiber 902 enables interrogation of a sample region with mid-infrared radiation even though the sample region is remote from source 116.

In similar fashion, optical fiber 904 is optically coupled between lens 908 and sample region 112. Lens 908 couples composite signal 124 from sample region 112 into the input facet of optical fiber 908, which conveys the composite signal to wavelength discriminator 118. As a result, wavelength discriminator 118 can also be remote from sample region 112.

It is to be understood that the disclosure teaches just one example of the illustrative embodiment and that many variations of the invention can easily be devised by those skilled in the art after reading this disclosure and that the scope of the present invention is to be determined by the following claims.

What is claimed is:

1. An apparatus comprising:
    (1) a spectrometer comprising;
        (i) a source operable for providing mid-infrared radiation to a sample region;
        (ii) a wavelength discriminator operable for receiving a composite light signal from the sample region and spatially dispersing the composite light signal as a plurality of wavelength signals; and
        (iii) a plurality of detectors, each of the plurality of detectors operable for generating one of a plurality of first electrical signals based on one of the plurality of wavelength signals; and
    (2) a sample holder, the sample holder being operable for locating a sample fluid at the sample region, the sample holder being dimensioned and arranged to enable the sample fluid to (a) receive mid-infrared radiation such that at least a portion of the mid-infrared radiation transits the sample fluid and (b) provide the composite light signal.

2. The apparatus of claim 1 wherein the sample holder includes a first region that is operable for drawing the sample fluid into the sample holder via capillary action.

3. The apparatus of claim 1 wherein the sample holder includes a sample cell that comprises work-hardened silver halide.

4. The apparatus of claim 3 wherein the sample cell includes a portion of a conduit that is operable for conveying the sample fluid through the sample region, the portion of the conduit comprising work-hardened silver halide.

5. The apparatus of claim 3 wherein the sample cell comprises a chamber operable for containing the sample fluid, the chamber comprising work-hardened silver halide.

6. The apparatus of claim 1 wherein at least one of the plurality of detectors comprises:
    (i) a plate, wherein the plate comprises an absorber operable for converting incident mid-infrared radiation to heat;
    (ii) an electrode disposed on a substrate, the electrode and the plate collectively defining a parallel-plate capacitor whose capacitance is based on a first separation between the electrode and the plate; and
    (iii) an actuator operable for changing the first separation in response to a change in the temperature of the actuator, the actuator comprising a first bi-material element having a first end and a second end, the first end being mechanically coupled with the plate and the second end being substantially immovable with respect to the substrate, wherein a change in the temperature of the first bi-material element induces motion of the first end with respect to the substrate;
    wherein the plate and the actuator are thermally coupled to enable transfer of heat from the plate to the actuator, and wherein the actuator and the substrate are thermally coupled to enable transfer of heat from the actuator to the substrate.

7. The apparatus of claim 1 wherein the source is dimensioned and arranged to provide the mid-infrared radiation as a pulse of mid-infrared radiation.

8. The apparatus of claim 7 wherein the source emits the mid-infrared radiation in response to a drive signal that is an electrical pulse.

9. The apparatus of claim 1 further comprising:
    (3) a processor; and
    (4) a database comprising a plurality of spectra for each of a first chemical constituent and a second chemical constituent, wherein the sample comprises the first chemical constituent and the second chemical constituent;
    wherein the processor is operable for receiving the plurality of wavelength signals and providing an output signal that is based on the plurality of wavelength signals and the plurality of spectra.

10. The apparatus of claim 1 further comprising:
    (3) a first optical fiber operable for conveying mid-infrared radiation, the first optical fiber comprising silver halide, the first optical fiber being operatively coupled with each of the source and the first region; and
    (4) a second optical fiber, the second optical fiber comprising silver halide, the second optical fiber operable for conveying the composite light signal from the first region to the wavelength discriminator.

11. An apparatus comprising:
    (1) a spectrometer comprising;
        (i) a source operable for providing mid-infrared radiation;
        (ii) a wavelength discriminator operable for spatially dispersing a composite light signal into a plurality of wavelength signals; and
        (iii) a plurality of detectors, each of the plurality of detectors operable for generating one of a plurality of first electrical signals based on one of the plurality of wavelength signals; and
    (2) a sample holder that includes a sample cell that comprises work-hardened silver halide, the sample holder operable for locating a sample fluid such that the sample fluid (a) receives mid-infrared radiation from the source such that at least a portion of the mid-infrared radiation transits the sample fluid and (b) provides the composite light signal to the wavelength discriminator such that the composite light signal includes the mid-infrared radiation and spectral information based on the sample fluid.

12. The apparatus of claim 11 wherein the sample cell includes a portion of a conduit that is operable for conveying the sample fluid through the sample region, the portion of the conduit comprising work-hardened silver halide.

13. The apparatus of claim 11 wherein the sample cell comprises a chamber operable for containing the sample fluid, the chamber comprising work-hardened silver halide.

14. The apparatus of claim 13 wherein the sample cell includes a first region that is operable for drawing the sample fluid into the sample holder via capillary action, the first region comprising work-hardened silver halide.

15. The apparatus of claim 11 further comprising:
    (3) a first optical fiber operable for conveying mid-infrared radiation, the first optical fiber comprising a first material that is substantially transparent for mid-infrared radiation, the first optical fiber being operatively coupled with each of the source and the first region; and
    (4) a second optical fiber, the second optical fiber comprising the first material, the second optical fiber operable for conveying the composite light signal from the first region to the wavelength discriminator.

16. An apparatus comprising:
    (1) a spectrometer comprising;
        (i) a source operable for providing mid-infrared radiation;

(ii) a first optical fiber operable for conveying mid-infrared radiation from the source to a sample region, the first optical fiber comprising silver halide;

(iii) a second optical fiber operable for conveying a composite light signal comprising mid-infrared radiation from the sample region to a wavelength discriminator, the second optical fiber comprising silver halide;

(iv) the wavelength discriminator, the wavelength discriminator being operable for receiving the composite light signal and spatially dispersing it as a plurality of wavelength signals; and (v) a plurality of detectors, each of the plurality of detectors operable for generating one of a plurality of first electrical signals based on one of the plurality of wavelength signals; and (2) a sample holder, the sample holder being operable for locating a sample fluid at the sample region, the sample holder being dimensioned and arranged to enable the sample fluid to (a) receive mid-infrared radiation such that at least a portion of the mid-infrared radiation transits the sample fluid and (b) provide the composite light signal.

17. The apparatus of claim 16 wherein the sample holder includes a sample cell that comprises work-hardened silver halide.

18. The apparatus of claim 17 wherein the sample cell includes a portion of a conduit that is operable for conveying the sample fluid through the sample region, the portion of the conduit comprising work-hardened silver halide.

19. The apparatus of claim 17 wherein the sample cell comprises a chamber operable for containing the sample fluid, the chamber comprising work-hardened silver halide.

20. The apparatus of claim 19 wherein the sample cell includes a first region that is operable for drawing the sample fluid into the sample holder via capillary action, the first region comprising work-hardened silver halide.

21. A method comprising:
locating a sample fluid in a sample region, the sample fluid including a first chemical constituent and a background solvent, the sample fluid being located by a sample holder that enables mid-infrared radiation to transit the sample fluid and enables the sample fluid to provide a composite light signal;
passing mid-infrared radiation through the sample fluid;
providing the composite light signal such that it includes spectral information based on each of a first chemical constituent and the background solvent;
distributing the first composite light signal into a plurality of wavelength signals; and
providing a first electrical signal based on the plurality of wavelength signals.

22. The method of claim 21 further comprising generating an output signal that is based on first electrical signal and a first spectral model, wherein the first spectral model is based on the mid-infrared spectral signature of the background solvent.

23. The method of claim 21 further comprising providing the infrared radiation, wherein the mid-infrared radiation is provided by operations comprising:
providing a drive signal to a source, wherein the source is dimensioned and arranged to convert the drive signal into mid-infrared radiation; and
modulating the drive signal such that it comprises a plurality of pulses of electrical energy.

24. The method of claim 21 further comprising providing a sample holder, wherein the sample holder includes a portion of a conduit that conveys the sample fluid to the sample region, the portion of the conduit comprising work-hardened silver halide.

25. The method of claim 21 further comprising providing a sample holder, wherein the sample holder includes a chamber that contains the sample fluid in the sample region, the chamber comprising work-hardened silver halide.

26. The method of claim 21 further comprising providing a sample holder, wherein the sample holder includes a first region that is operable for drawing the sample fluid into the sample holder via capillary action, the first region comprising work-hardened silver halide.

27. The method of claim 21 wherein the sample fluid is exposed to mid-infrared radiation by operations comprising:
providing a drive signal to a source, wherein the source converts the drive signal into mid-infrared radiation; and
conveying mid-infrared radiation from the source to the sample region via a first optical fiber that comprises a first material that is substantially transparent for mid-infrared radiation.

28. The method of claim 27 further comprising providing the first optical fiber such that the first material comprises silver halide.

29. The method of claim 21 wherein the composite light signal is distributed into the plurality of wavelength signals by operations comprising:
coupling the composite light signal into a first optical fiber at the sample region, the first optical fiber comprising a first material that is substantially transparent for mid-infrared radiation, wherein the first optical fiber is optically coupled with a wavelength discriminator operative to spatially disperse the composite light signal into the plurality of wavelength signals; and
emitting the composite light signal from the first optical fiber such that it is received by the wavelength discriminator.

30. The method of claim 29 further comprising providing the first optical fiber such that the first material comprises silver halide.

* * * * *